(12) United States Patent
Zeng et al.

(10) Patent No.: US 12,725,354 B2
(45) Date of Patent: Sep. 1, 2026

(54) METHOD FOR IMAGE GENERATION BASED ON ORAL IMAGING AND SYSTEM THEREOF

(71) Applicant: Guangzhou Institute of Cancer Research, the Affiliated Cancer Hospital, Guangzhou Medical University, Guangzhou (CN)

(72) Inventors: Yu Zeng, Guangzhou (CN); Zhiwei Liao, Guangzhou (CN); Linjing Wang, Guangzhou (CN); Bin Qi, Guangzhou (CN); Xiaowei Zhang, Guangzhou (CN)

(73) Assignee: GUANGZHOU INSTITUTE OF CANCER RESEARCH, THE AFFILIATED CANCER HOSPITAL, GUANGZHOU MEDICAL UNIVERSITY, Guangzhou (CN)

( * ) Notice: Subject to any disclaimer, the term of this patent is extended or adjusted under 35 U.S.C. 154(b) by 0 days.

(21) Appl. No.: 19/180,265

(22) Filed: Apr. 16, 2025

(65) Prior Publication Data

US 2026/0134617 A1 May 14, 2026

Related U.S. Application Data

(63) Continuation of application No. PCT/CN2024/071919, filed on Jan. 12, 2024.

(30) Foreign Application Priority Data

Jul. 12, 2023 (CN) ........................ 202310848525.X

(51) Int. Cl.
*G06T 17/00* (2006.01)
*A61B 6/00* (2024.01)
(Continued)

(52) U.S. Cl.
CPC .............. *G06T 17/00* (2013.01); *A61B 6/032* (2013.01); *A61B 6/4085* (2013.01); *A61B 6/51* (2024.01);
(Continued)

(58) Field of Classification Search
CPC .................. G06T 17/00; G06T 7/0012; G06T 2207/10081; G06T 2207/30008;
(Continued)

(56) References Cited

U.S. PATENT DOCUMENTS

2014/0329194 A1* 11/2014 Sachdeva .............. A61C 7/002 433/24
2018/0153646 A1* 6/2018 Sachdeva .............. A61C 7/002

FOREIGN PATENT DOCUMENTS

CN 108269294 A 7/2018
CN 111583219 A 8/2020
(Continued)

OTHER PUBLICATIONS

Jiang CN 111583219 A (Year: 2020).*
(Continued)

*Primary Examiner* — Devona E Faulk
*Assistant Examiner* — Donna J. Ricks
(74) *Attorney, Agent, or Firm* — Leong C. Lei

(57) ABSTRACT

A method for generating images includes: acquiring CT image data of an oral cavity, and then constructing an oral skeletal model based on this; extracting skeletal features of the oral skeletal model, and covering the oral skeletal model with soft tissues to obtain a first oral cavity model; carrying out laser three-dimensional scanning on the treated oral cavity to construct a second oral cavity model, and comparing the first oral cavity model with the second oral cavity model, and marking the soft tissue difference area in the second oral cavity model; acquiring optical image informa-
(Continued)

tion of a target acquisition area in an oral cavity, and extracting soft tissue features from the optical image information; covering the extracted soft tissue features in the second oral cavity model to obtain a three-dimensional image model of the oral cavity, and acquiring oral images from the three-dimensional image model to generate oral images.

4 Claims, 4 Drawing Sheets

(51) Int. Cl.

| | |
|---|---|
| ***A61B 6/03*** | (2006.01) |
| ***A61B 6/40*** | (2024.01) |
| ***A61B 6/51*** | (2024.01) |
| ***G06T 7/00*** | (2017.01) |

(52) U.S. Cl.
CPC .......... *A61B 6/5247* (2013.01); *G06T 7/0012* (2013.01); *G06T 2207/10081* (2013.01); *G06T 2207/30008* (2013.01); *G06T 2207/30036* (2013.01); *G06T 2210/41* (2013.01)

(58) Field of Classification Search
CPC ....... G06T 2207/30036; G06T 2210/41; A61B 6/032; A61B 6/4085; A61B 6/51; A61B 6/5247
See application file for complete search history.

(56) References Cited

FOREIGN PATENT DOCUMENTS

| | | | |
|---|---|---|---|
| CN | 113052902 | A | 6/2021 |
| CN | 114261095 | A | 4/2022 |
| CN | 115886863 | A | 4/2023 |
| CN | 117058309 | A | 11/2023 |
| WO | 2018096155 | A1 | 5/2018 |
| WO | 2023274690 | A1 | 1/2023 |

OTHER PUBLICATIONS

Retrieval report—First search dated Jan. 1, 2024 in SIPO application No. 202310848525.X.
Notice of first Office action dated Jan. 2, 2024 in SIPO application No. 202310848525.X.
Notification to Grant Patent Right for Invention dated Mar. 25, 2024 in SIPO application No. 202310848525.X.
International Search Report issued in corresponding PCT Application No. PCT/CN2024/071919 dated Mar. 27, 2024.

* cited by examiner

METHOD FOR IMAGE GENERATION BASED ON ORAL IMAGING AND SYSTEM THEREOF

CROSS-REFERENCE TO RELATED APPLICATIONS

This application is a continuation of PCT/CN 2024/071919, filed on Jan. 12, 2024 and claims priority to Chinese Patent Application No. 202310848525.X, filed on Jul. 12, 2023, the contents of which are hereby incorporated by reference.

TECHNICAL FIELD

The application relates to the technical field of image processing, in particular to a method for image generation based on oral imaging and a system thereof.

BACKGROUND

Oral examination and treatment are an indispensable part of the treatment of head and neck tumors, especially before radiotherapy and during follow-up. Additionally, throughout the anti-tumor treatment, the diagnosis and treatment of oral complications in the course of anti-tumor therapy require imaging analysis of the patient's crown, root, periapical tissue and jawbones to better assist doctors in the diagnosing oral diseases and determining treatment plans.

At present, image sensors with X-ray recognition or oral CBCT combined with digital processing output circuits are used for oral imaging to transmit digital signals to a computer, and either two-dimensional or three-dimensional image data are presented by application software. However, in the prior art, the image sensor for X-ray identification or oral CT scan may only obtain hard tissue structures such as teeth and jawbones in the oral cavity, while X-rays and oral CT have strong penetration to soft tissues that makes it impossible to accurately identify the relevant soft tissues of muscles and/or tumors in the oral cavity. If optical imaging technology is used for oral cavity imaging, it can be easily affected by the complex three-dimensional structure of the oral cavity, resulting in limited field of view, tissue occlusion, and insufficient illumination that ultimately leads to the inability to collect clear and accurate images of the complete tissue structure in the oral cavity. Consequently, it is necessary to collect and splice images of the muscle tissue from various angles, but the spliced images may only display two-dimensional oral images and cannot accurately and completely display the overall condition of the soft tissues. As a result, the obtained oral images are unable to accurately display the actual oral conditions of the patient.

Therefore, there is an urgent need for a method to improve the accuracy, clarity and reconstruction of oral imaging for the diagnosis and treatment of oral diseases.

SUMMARY

The disclosure provides a method for image generation based on oral imaging and a system thereof to solve the technical problems of poor clarity, limited accuracy, and inadequate reconstruction of oral imaging in the prior art.

In order to solve the above technical problems, embodiments of the disclosure provide a method for image generation based on oral imaging, which includes:

acquiring CT image data of an oral cavity to be treated, and constructing an oral skeletal model based on the CT image data;

extracting skeletal features of the oral skeletal model, and covering the oral skeletal model with soft tissues based on the skeletal features through a preset healthy soft and hard tissue oral cavity model database to obtain a first oral cavity model; where the preset healthy soft and hard tissue oral cavity model database stores oral cavity models with healthy soft and hard tissues;

carrying out laser three-dimensional scanning on the oral cavity to be treated to construct a second oral cavity model, and comparing the first oral cavity model with the second oral cavity model to obtain a soft tissue difference area between the first oral cavity model and the second oral cavity model, and marking the soft tissue difference area in the second oral cavity model;

acquiring optical image information of a target acquisition area in an oral cavity to be treated, and extracting soft tissue features from the optical image information; where the target acquisition area corresponds to the soft tissue difference area marked on the second oral cavity model; and covering the extracted soft tissue features in the second oral cavity model to obtain a three-dimensional image model of the oral cavity to be treated and then acquiring oral images from the three-dimensional image model to generate oral images.

Optionally, acquiring CT image data of an oral cavity to be treated, and constructing an oral skeletal model based on the CT image data includes:

scanning the oral cavity to be treated layer by layer in a sequential manner by using the cone-beam imaging device according to the preset scanning interval to obtain CT image data corresponding to each layer, where the scanning interval is adjusted based on penetration depth to enhance image precision;

performing skeletal hard tissue identification on each scanned cross-sectional layer of CT image data and extracting hard tissue feature model data layer by layer, where the extracted data represents the skeletal structure at that specific depth;

sequentially correcting the hard tissue feature model data extracted from the corresponding CT image data of each layer, so that in the process of modifying the hard tissue feature model data of one layer each time, the hard tissue feature model data adjacent to the layer is taken as the modified reference model data, and the modified reference model data and the hard tissue feature model data of the adjacent layers are combined and merged, so as to detect the first edge smoothness between the combined modified reference model data and the hard tissue feature model data of the layer, and then modify the hard tissue feature model data of the layer according to the first edge smoothness; and combining and merging the modified hard tissue feature model data of each layer to construct the oral skeletal model.

Optionally, modifying the hard tissue feature model data of the layer according to the first edge smoothness includes:

when the first edge smoothness between adjacent layers is within the preset threshold interval, modification of the hard tissue feature model data of the layer is not required;

when the first edge smoothness is outside a preset threshold interval, calculating a second edge smoothness between the hard tissue feature model data of each layer in the modified reference model data, and when the difference between the first edge smoothness and the second edge smoothness is greater than a preset error, smoothing and modifying the edge of the hard tissue feature model data of the layer according to the second edge smoothness, so as to complete the modification of the hard tissue feature model data of the layer; and repeating the process until all the hard tissue feature model data of each layer has been modified.

Optionally, extracting the skeletal features of the oral skeletal model, and covering the oral skeletal model with soft tissues based on the skeletal features through a preset healthy soft and hard tissue oral cavity model database to obtain a first oral cavity model includes:

extracting skeletal features of preset key areas in the oral skeletal model; where the preset key areas include maxillary area, mandibular area, maxillary alveolar bone area and mandibular alveolar bone area;

retrieving from the preset healthy soft and hard tissue oral cavity model database, and using a soft and hard tissue oral cavity model with the greatest similarity to the skeletal features of the preset key areas as a reference model; where the healthy soft and hard tissue oral cavity model database prestores a plurality of different soft and hard tissue oral cavity models corresponding to the skeletal features of preset key areas; and extracting the soft tissue data of the reference model and overlaying the soft tissue data on the oral skeletal model to construct a first oral cavity model.

Optionally, carrying out laser three-dimensional scanning on the treated oral cavity to construct a second oral cavity model, and comparing the first oral cavity model with the second oral cavity model, so as to obtain the soft tissue difference area between the first oral cavity model and the second oral cavity model, and marking the soft tissue difference area in the second oral cavity model includes:

carrying out laser three-dimensional scanning on the oral cavity to be treated to obtain an oral cavity structure model;

matching the oral skeletal model with the oral cavity structure to construct a second oral cavity model;

comparing the first oral cavity model with the second oral cavity model to sequentially obtain the areas with different structures between the first oral cavity model and the second oral cavity model;

if the area of the structural difference exists in the first oral cavity model, the difference area is eliminated; and if the area of the structural difference exists in the second oral cavity model, the difference area is designated as a soft tissue difference area and marked in the second oral cavity model.

Optionally, acquiring the optical image information of the target acquisition area in the oral cavity to be treated, and extracting the soft tissue features from the optical image information includes:

acquiring optical image information of the target acquisition area in the oral cavity to be treated, and sequentially carrying out pathological identification on the optical image information according to the pathological identification model; where the target acquisition area corresponds to the soft tissue difference area marked on the second oral cavity model; and identifying the optical image information to detect pathological features of soft tissues, so as to extract the soft tissue feature data with pathological features.

Optionally, covering the extracted soft tissue features in the second oral cavity model to obtain a three-dimensional image model of the oral cavity to be treated specifically includes:

covering the extracted soft tissue feature data with pathological features in a second oral cavity model at the corresponding area sequentially according to the target acquisition area of the optical image information with pathological features;

identifying and removing the soft tissue difference areas corresponding to the optical image information without pathological features in the second oral cavity model to obtain the final second oral cavity model; and using the soft tissue data in the first oral cavity model, covering the unmarked areas in the final second oral cavity model with soft tissue, so as to obtain a three-dimensional image model of the oral cavity to be treated.

Correspondingly, the disclosure also provides a system for image generation based on oral imaging, including an acquisition device and a processing host; the acquisition device includes a cone-beam imaging device, a laser three-dimensional scanner and an optical image acquisition device;

the processing host includes a CT image module, a first oral cavity model module, a second oral cavity model module, a soft tissue feature module and a soft tissue covering module;

the CT image module is configured to acquire CT image data of an oral cavity to be treated, and constructing an oral skeletal model from the CT image data;

the first oral cavity model module is configured to for extracting the skeletal features of the oral cavity skeletal model, and covering the oral cavity skeletal model with soft tissues using the skeletal features from a preset oral cavity model database with healthy soft and hard tissues to obtain a first oral cavity model; where the preset oral cavity model database with healthy soft and hard tissues stores oral cavity models containing healthy soft and hard tissues;

the second oral cavity model module is configured to carry out laser three-dimensional scanning on the oral cavity to be treated, so as to construct a second oral cavity model, and comparing the first oral cavity model with the second oral cavity model to obtain a soft tissue difference area between them, and then mark the soft tissue difference area in the second oral cavity model;

the soft tissue feature module is configured to acquire optical image information of a target acquisition area in an oral cavity to be treated, and extracting soft tissue features from the optical image information; where the target acquisition area corresponds to the soft tissue difference area marked on the second oral cavity model;

the soft tissue covering module is configured to cover the extracted soft tissue features into the second oral cavity model to obtain a three-dimensional image model of the oral cavity to be treated, and then generate oral images from the three-dimensional image model to generate oral images.

Correspondingly, the disclosure also provides a terminal device, including a processor, a memory and a computer program stored in the memory and configured to be executed by the processor. The processor, when executing the computer program, is configured to detect at least one area of interest in each of the analyzed oral images, where the area of interest includes one or more pathological soft tissue characteristics or skeletal anomalies. The processor further generates a composite three-dimensional oral model by overlaying two or more of the CT image data, laser three-dimensional scan data, and optical image data, and identifying the at least one area of interest from each respective image in the composite model.

Correspondingly, the disclosure also provides a computer-readable storage medium, the computer-readable storage medium includes a stored computer program; the computer program controls the device where the computer-readable storage medium is located while executing the method for image generation based on oral imaging according to any of the above.

Compared with the prior art, the embodiments of the disclosure have the following beneficial effects:

according to the technical schemes of the disclosure, the soft tissue difference area between them is obtained by comparing the oral CT image covered with soft tissue with the second oral cavity model of laser three-dimensional scanning; and the soft tissue in the soft tissue difference area is covered with actual feature data by combining with the optical image information, so that the three-dimensional image model of the oral cavity to be treated is accurately obtained, and the corresponding oral image is generated through the three-dimensional image model. This method involves oral imaging and includes steps such as CT scanning, 3D laser scanning, and optical image analysis. It utilizes a cone-beam imaging device with dynamic interval adjustment based on penetration depth to enhance scanning precision. Additionally, it synthesizes skeletal images by detecting and adjusting edge smoothness inconsistencies, reducing distortion, and improving diagnosis by integrating multi-modal imaging. This approach provides a more precise 3D anatomical model for medical use, aiding in the accurate identification of pathological changes in oral tissues. By integrating these advancements, the disclosure avoids the collection and analysis of pathological soft tissues such as muscles and/or tumors solely through optical images, which would otherwise require image splicing in cases of multiple optical image data—an approach prone to image distortion. Furthermore, two-dimensional optical images cannot provide structural information of specific pathological soft tissues such as muscles and/or tumors, whereas the three-dimensional image model of the disclosure can accurately and clearly restore the structural information of the oral cavity to be treated. Therefore, the disclosure achieves a high degree of anatomical accuracy and is convenient for doctors to analyze the pathological conditions of the oral cavity.

DETAILED DESCRIPTION OF THE EMBODIMENTS

The technical schemes in the embodiments of the disclosure will be clearly and completely described with reference to the attached figures. Obviously, the described embodiments are only a part of the embodiments of the disclosure, but not the whole embodiments. Based on the embodiments in the disclosure, all other embodiments obtained by ordinary technicians in the field without creative work belong to the scope of protection of the disclosure.

Figure 1:
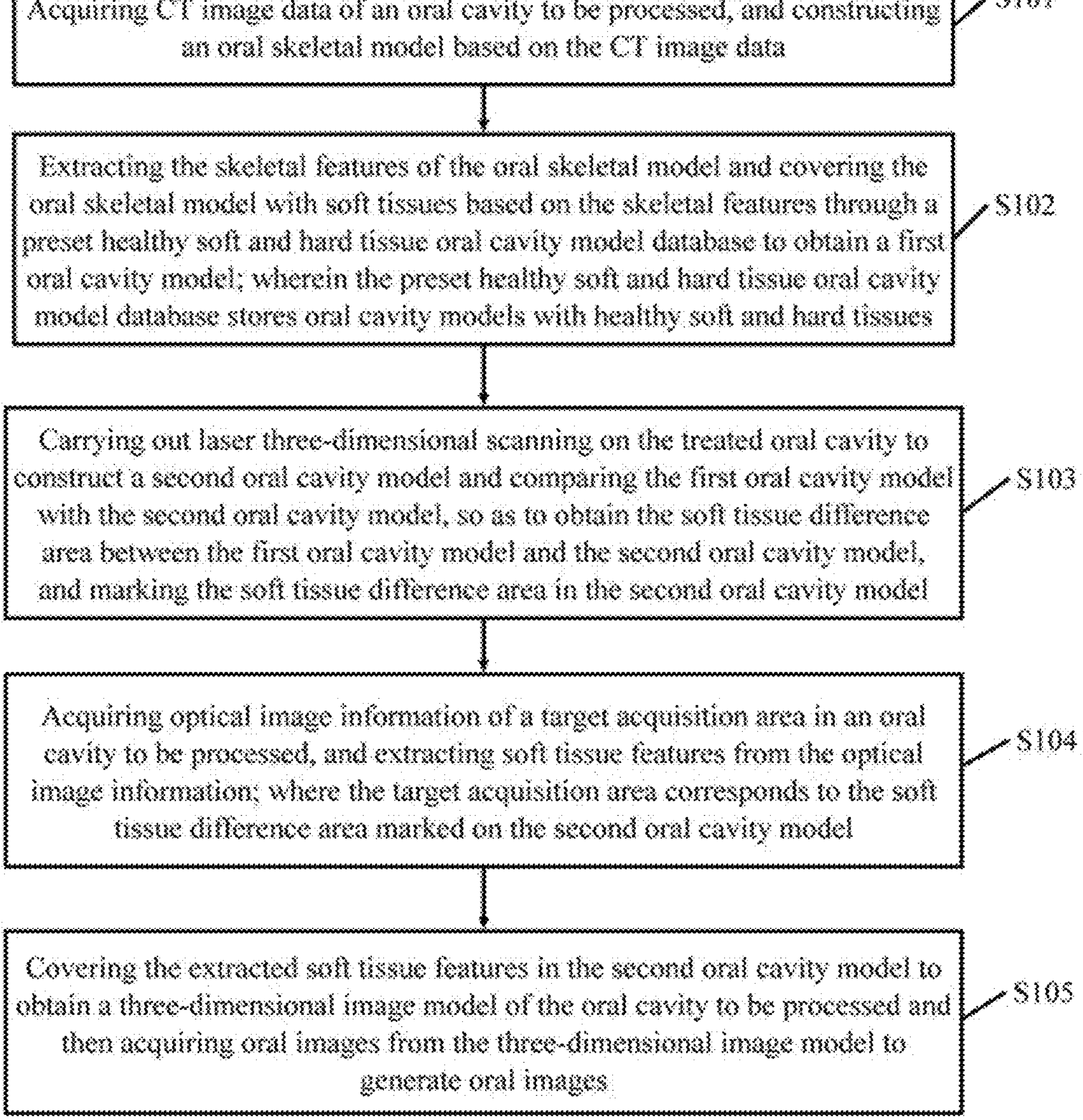
FIG. 1 shows a flowchart of a method for image generation based on oral imaging provided by the embodiments of the disclosure.

Embodiment One, referring to FIG. 1, a method for image generation based on oral imaging provided by the embodiments of the disclosure, which includes the following steps S101-S105:

Step S101: acquiring CT image data of an oral cavity to be treated, and constructing an oral skeletal model based on the CT image data.

It should be noted that the embodiments of the disclosure mainly used for oral image treating with soft tissue abnormalities in the oral cavity to be treated, not for oral imaging treating with hard tissues such as skeletons, so the image generation method based on oral imaging in the embodiments of the disclosure is mainly used for soft tissue abnormalities such as tumors and/or muscles.

Optionally, acquiring CT image data of an oral cavity to be treated, and constructing an oral skeletal model based on the CT image data includes:

scanning the oral cavity to be treated layer by layer by cone-beam imaging device according to the preset scanning interval to obtain CT image data corresponding to each layer; carrying out skeletal hard tissue identification on CT image data corresponding to each layer, and extracting hard tissue feature model data corresponding to each CT image data; sequentially correcting the hard tissue feature model data extracted from the corresponding CT image data of each layer, so that in the process of modifying the hard tissue feature model data of one layer each time, the hard tissue feature model data adjacent to the layer is taken as the modified reference model data, and the modified reference model data and the hard tissue feature model data of the layer are combined and merged, so as to calculate the first edge smoothness between the combined modified reference model data and the hard tissue feature model data of the layer, and then modify the hard tissue feature model data of the layer according to the first edge smoothness; synthesizing a refined skeletal model by detecting and correcting edge smoothness inconsistencies across all layers to improve anatomical accuracy; and combining and merging the modified hard tissue feature model data of each layer to construct the oral skeletal model; where an oral device is provided for sensing various biological features, including temperature, pH, electromyographic signal, muscle thickness, blood flow status or other conditions in the oral cavity, and an interface device cooperatively coupled to the oral appliance is configured to transfer information of the biological features to a receiving device external to the oral cavity or to remove the device itself for external analysis.

In this embodiment, the cone-beam imaging device can scan the oral cavity to be treated layer by layer, and then obtain CT image data corresponding to each layer. The scanning interval can be set according to the scanning penetration ability of the cone-beam imaging device and the actual image requirements of the oral cavity to be treated, and the meaning of the scanning interval is the distance between the CT image data of each layer.

Further, scanning the oral cavity to be treated layer by layer can be understood as acquiring the oral cavity to be treated as acquiring the oral cavity profile layer by layer according to a certain distance (scanning interval), and the CT image data of each layer represent the oral cavity profile to be treated.

In this embodiment, by training the model to identify the skeletal structures from the CT image data in advance, the identification of the skeletal hard tissue from the corresponding CT image data of each layer can be realized, that is, a large number of training sets and test sets of CT image data containing skeletal information can be used to train the skeletal hard tissue identification model, so that the skeletal hard tissue corresponding to CT image data of each layer can be quickly and accurately identified, and thus the hard tissue feature model data corresponding to each CT image data can be extracted.

Figure 2:
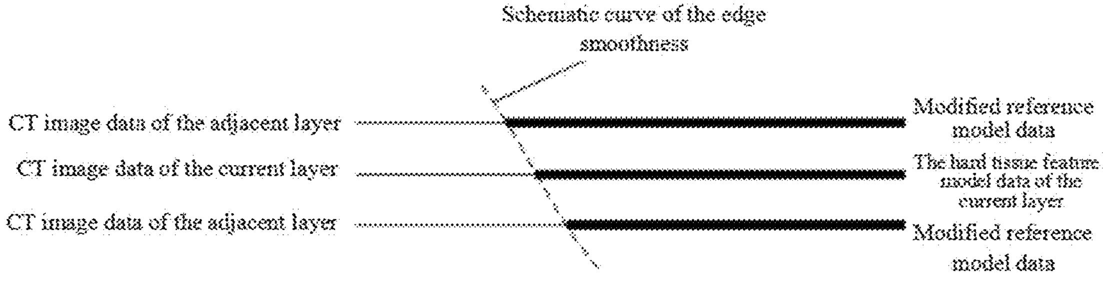
FIG. 2 shows a schematic diagram of the hard tissue feature model data of each layer provided by the embodiments of the disclosure.

In this embodiment, the hard tissue feature model data extracted from the corresponding CT image data of each layer are modified sequentially, so that in the process of modifying the hard tissue feature model data of one layer each time, it is necessary to use the hard tissue feature model data of the adjacent two layers or one layer as the reference model data for modification; then, by merging the modified reference model data with the current hard tissue feature model data of this layer, the edge smoothness between the two layers of hard tissue feature model data in the modified reference model data and the current hard tissue feature model data of this layer (three layers of hard tissue feature model data in total) can be obtained, as shown in FIG. 2; or, the edge smoothness between the hard tissue feature model data of a layer in the modified reference model data and the current hard tissue feature model data of this layer is obtained. This only applies to the first or last layer of all data.

In this embodiment, the edge smoothness can be calculated by the distance between corresponding edge data points in each layer. Since CT image data is obtained through the same cone-beam imaging device, the CT image data of each layer is aligned within the same coordinate system, which can be assigned to the hard tissue feature model data in each layer to obtain the position information of data points, thus accurately and quickly calculating the edge smoothness between each layer.

Optionally, modifying the hard tissue feature model data of the layer according to the first edge smoothness includes:

when the first edge smoothness is within the preset threshold interval, there is no need to modify the hard tissue feature model data of the layer; when the first edge smoothness is outside a preset threshold interval, calculating a second edge smoothness between the hard tissue feature model data of each layer in the modified reference model data, and when the difference between the first edge smoothness and the second edge smoothness is greater than a preset error, smoothing and modifying the edge of the hard tissue feature model data of the layer according to the second edge smoothness, so as to complete the modification of the hard tissue feature model data of the layer; until all layers have been modified.

In this embodiment, when the first edge smoothness is within the preset threshold range, it indicates that the hard tissue feature model data of each layer in the modified reference model data, compared to the hard tissue feature model data of the current layer, conforms to the normal skeletal condition of the oral cavity; therefore, there is no need to modify the hard tissue feature model data of the current layer.

In this embodiment, when the first edge smoothness is outside the preset threshold interval, it indicates that the hard tissue feature model data of each layer in the modified reference model data does not match the normal skeletal condition of the oral cavity compared to the hard tissue feature model data of the current layer; therefore, it is necessary to calculate the second edge smoothness between the hard tissue feature model data of the two layers in the modified reference model data to smooth and modify the edges of the hard tissue feature model data of that layer. Furthermore, the edges of the hard tissue feature model data in this layer can be smoothed and modified by taking the average data points between the hard tissue feature model data in the modified reference model data as the reference value for smoothing and modifying the edges of the hard tissue feature model data in this layer. At the same time, the CT image data of the oral cavity to be treated can be recalculated to ensure that errors are not caused by acquisition devices.

Furthermore, when the first edge smoothness of the reacquired CT image data is still outside the preset threshold interval, it indicates that there is still an abnormality in the hard tissue of the oral cavity to be treated, and a corresponding message is generated for alarm output.

Furthermore, if the current layer is in the first or last layer of all data, as it is the starting or ending layer, its hard tissue feature model data in CT image data serves as a data feature point. Therefore, there will be no situation where the first edge smoothness is outside the preset threshold interval in the first or last layer of CT image data Step 102: extracting the skeletal features of the oral skeletal model and covering the oral skeletal model with soft tissues based on the skeletal features through a preset healthy soft and hard tissue oral cavity model database to obtain a first oral cavity model; where the preset healthy soft and hard tissue oral cavity model database stores oral cavity models with healthy soft and hard tissues.

Optionally, extracting the skeletal features of the oral skeletal model, and covering the oral skeletal model with soft tissues based on the skeletal features through a preset healthy soft and hard tissue oral cavity model database to obtain a first oral cavity model includes:

extracting skeletal features of preset key areas in the oral skeletal model; where these preset key areas include the maxillary area, mandibular area, maxillary alveolar bone area and mandibular alveolar bone area; in a preset healthy soft and hard tissue oral cavity model database, a soft and hard tissue oral cavity model with the greatest similarity to the skeletal features of the preset key area is retrieved as a reference model; where the healthy soft and hard tissue oral cavity model database prestores a plurality of different soft and hard tissue oral cavity models corresponding to the skeletal features of preset key areas; and extracting the soft tissue data of the reference model, and overlaying the soft tissue data on the oral skeletal model to construct a first oral cavity model.

In this embodiment, by using a pretrained skeletal identification model, it is possible to quickly and accurately extract the skeletal features of the preset key areas in the oral skeletal model. Skeletal features refer to the skeletal structural features that can reflect the details of the skeletal structure, including the distance and curvature between feature points during the skeletal identification process. Furthermore, by extracting the skeletal features of the preset key areas in the oral skeletal model, the soft and hard tissue oral cavity model with the highest similarity to the skeletal features of the preset key areas can be retrieved from the preset healthy soft and hard tissue oral cavity model database and used as a reference model for soft tissue coverage.

The soft and hard tissue oral cavity model includes both soft tissue data and hard tissue data (including skeletons); therefore, the corresponding soft and hard tissue oral cavity model can be determined through skeletal feature data, and the soft tissue in the determined soft and hard tissue oral cavity model can be covered onto the oral skeletal model to ensure the accuracy and feasibility of the comparative model used as a standard healthy soft tissue reference in the first oral cavity model.

In this embodiment, by extracting the soft tissue data of the reference model and covering the soft tissue data on the oral skeletal model, the first oral cavity model can be quickly and accurately constructed.

Step 103: carrying out laser three-dimensional scanning on the treated oral cavity to construct a second oral cavity model and comparing the first oral cavity model with the second oral cavity model, so as to obtain the soft tissue difference area between the first oral cavity model and the second oral cavity model, and marking the soft tissue difference area in the second oral cavity model.

Optionally, carrying out laser three-dimensional scanning on the treated oral cavity to construct a second oral cavity model, and comparing the first oral cavity model with the second oral cavity model, so as to obtain the soft tissue difference area between the first oral cavity model and the second oral cavity model, and marking the soft tissue difference area in the second oral cavity model includes:

carrying out laser three-dimensional scanning on the oral cavity to be treated to obtain an oral cavity structure; matching the oral skeletal model with the oral structure to construct a second oral cavity model; comparing the first oral cavity model with the second oral cavity model to sequentially obtain areas with different structures between the first oral cavity model and the second oral cavity model; if the area of the different structure exists in the first oral cavity model, the area of the different structure is eliminated; if the area of the different structure exists in the second oral cavity model, the area of the different structure is taken as a soft tissue difference area and marked in the second oral cavity model.

In this embodiment, the oral structure is obtained by performing laser three-dimensional scanning on the oral cavity to be treated. It can be understood that the principle of laser three-dimensional scanning is to construct an oral structure by emitting laser and receiving reflected laser information, therefore, this oral structure model cannot accurately express the specific pathological conditions of soft tissue, and can only reflect the specific oral structural characteristics (including the size, structure, and position of soft tissue), but cannot reflect the condition or pathological changes of the soft tissue.

In this embodiment, through the obtained oral structure, the oral skeletal model can be combined with the oral structure; since the oral structure model represents the specific structural information of the oral cavity to be treated, the skeletal data in the oral skeletal model can accurately ensure the structural integrity of the oral structure. When the oral skeletal model is combined with the oral structure, there may be a situation where the oral skeletal model is exposed, indicating that the oral skeleton and the oral structure are not based on the same data to be treated in the oral cavity, and there may be issues with the devices or acquiring process that require manual confirmation by the operator, and with their cooperation, a second oral cavity model can be constructed.

In this embodiment, by comparing the second oral cavity model with the first oral cavity model, the areas where there are differences in soft tissue structure (including the size and position of soft tissue) between the two can be obtained. However, when the area of different structure exists in the first oral cavity model, since the first oral cavity model is based on data information of a healthy oral cavity, the different structure may be a problem of missing oral soft tissue that needs to be restored, which is not within the scope of tumor detection and diagnosis, and therefore needs to be eliminated; for the different structures in the second oral cavity model, they represent the extra soft tissue structures in the treated oral soft tissue compared to healthy oral tissue, which may indicate abnormal oral soft tissue, therefore, it is necessary to designate these areas as soft tissue difference area and mark them in the second oral cavity model.

Step 104: acquiring optical image information of a target acquisition area in an oral cavity to be treated, and extracting soft tissue features from the optical image information; where the target acquisition area corresponds to the soft tissue difference area marked on the second oral cavity model.

Optionally, acquiring the optical image information of the target acquisition area in the oral cavity to be treated, and extracting the soft tissue features from the optical image information includes:

acquiring optical image information of the target acquisition area in the oral cavity to be treated, and sequentially carrying out pathological identification on the optical image information according to the pathological identification model; where the target acquisition area corresponds to the soft tissue difference area marked on the second oral cavity model; identifying the optical image information with pathological features to identify the soft tissue features, so as to extract the soft tissue feature data with pathological features.

In this embodiment, by acquiring the optical image information of the target acquisition area in the oral cavity to be treated, the pathological structure information of the soft tissue surface corresponding to the soft tissue difference area on the second oral cavity model can be obtained, so that the optical image information with pathological features can be accurately identified to extract the soft tissue feature data with pathological features.

Step 105: covering the extracted soft tissue features in the second oral cavity model to obtain a three-dimensional image model of the oral cavity to be treated and then acquiring oral images from the three-dimensional image model to generate oral images.

Optionally, covering the extracted soft tissue features on the second oral cavity model to obtain a three-dimensional image model of the oral cavity to be treated specifically includes:

covering the extracted soft tissue feature data with pathological features in a second oral cavity model at the corresponding area sequentially according to the target acquisition area of the optical image information with pathological features; labeling and eliminating the soft tissue difference areas corresponding to the optical image information without pathological features in the second oral cavity model to obtain the final second oral cavity model; according to the soft tissue data in the first oral cavity model, the unlabeled areas in the final second oral cavity model are covered with soft tissue, so as to obtain a three-dimensional image model of the oral cavity to be treated.

In this embodiment, according to the target acquisition area of the optical image information with pathological features, the extracted soft tissue feature data with pathological features can be sequentially covered in the second oral cavity model, that is, the marked area is covered with soft tissue feature data with pathological features, so that the second oral cavity model can display the soft tissue structure with pathological features in three dimensions.

Further, in the second oral cavity model, the marked soft tissue difference areas corresponding to the optical image information without pathological features are eliminated to obtain the final second oral cavity model, so as to ensure that other unmarked areas of the second oral cavity model can be covered by soft tissues, and further ensure that the finally obtained three-dimensional image model of the oral cavity to be treated can restore the oral cavity to the greatest extent and take the oral cavity to be treated as a three-dimensional digital model, so that it can be displayed in the computer, which is convenient for doctors to analyze the pathology of the oral cavity to be treated, and at the same time, it also avoids the situation that the clear and accurate images of the oral cavity cannot be collected due to insufficient lighting points.

In this embodiment, by generating the corresponding three-dimensional image model, the problems of blurring and limited accuracy of oral images caused by insufficient lighting points can be avoided, and at the same time, the three-dimensional image model can be reused for many times without acquiring oral images for many times as required in the prior art, so that the accuracy of oral image generation is improved, the convenience for doctors to obtain oral images is improved, and the use experience is improved.

The implementation of the above embodiments has the following effects:

according to the technical schemes of the disclosure, the soft tissue difference area between them is obtained by comparing the oral CT image data covered with soft tissue with the second oral cavity model of laser three-dimensional scanning; and the soft tissue in the soft tissue difference area is covered with actual feature data by combining with the optical image information, so that the three-dimensional image model of the oral cavity to be treated is accurately obtained, and the corresponding oral image is generated through the three-dimensional image model; it avoids the collection and analysis of pathological soft tissues such as muscles and/or tumors only through optical images, resulting in the need for image splicing in the case of multiple optical image data, which is prone to image distortion; meanwhile, two-dimensional optical images cannot provide structural information of specific pathological soft tissues such as muscles and/or tumors, while the three-dimensional image model of the disclosure can accurately and clearly restore the structural information of the oral cavity to be treated, therefore, the disclosure has a high degree of reduction and is convenient for doctors to analyze the pathological conditions of the oral cavity.

Figure 3:
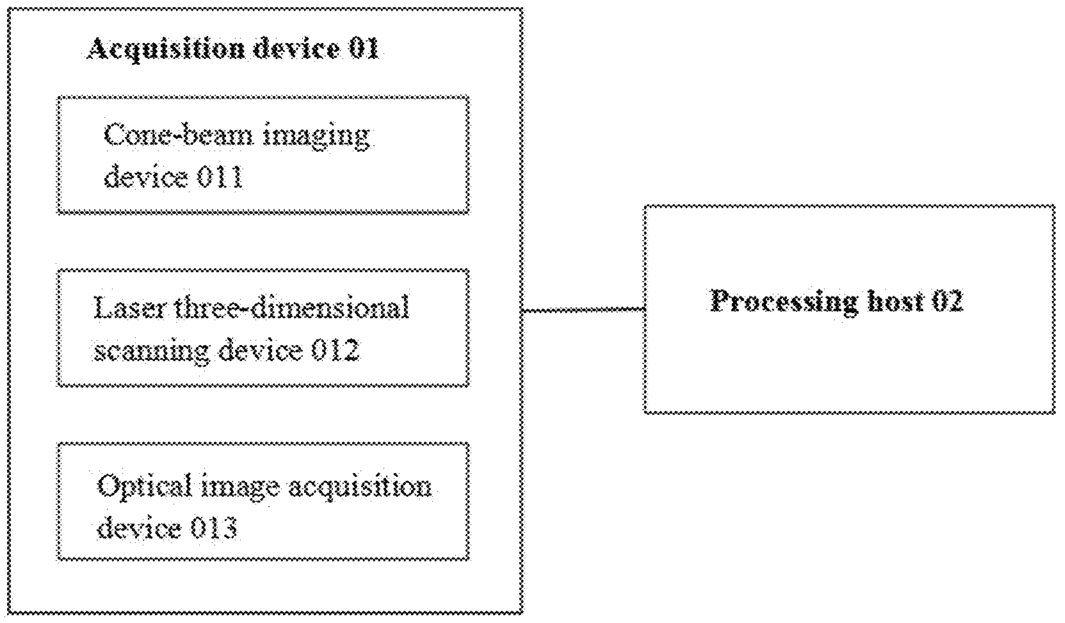
FIG. 3 shows a schematic structural diagram of a system for image generation based on oral imaging provided by the embodiments of the disclosure.
Figure 4:
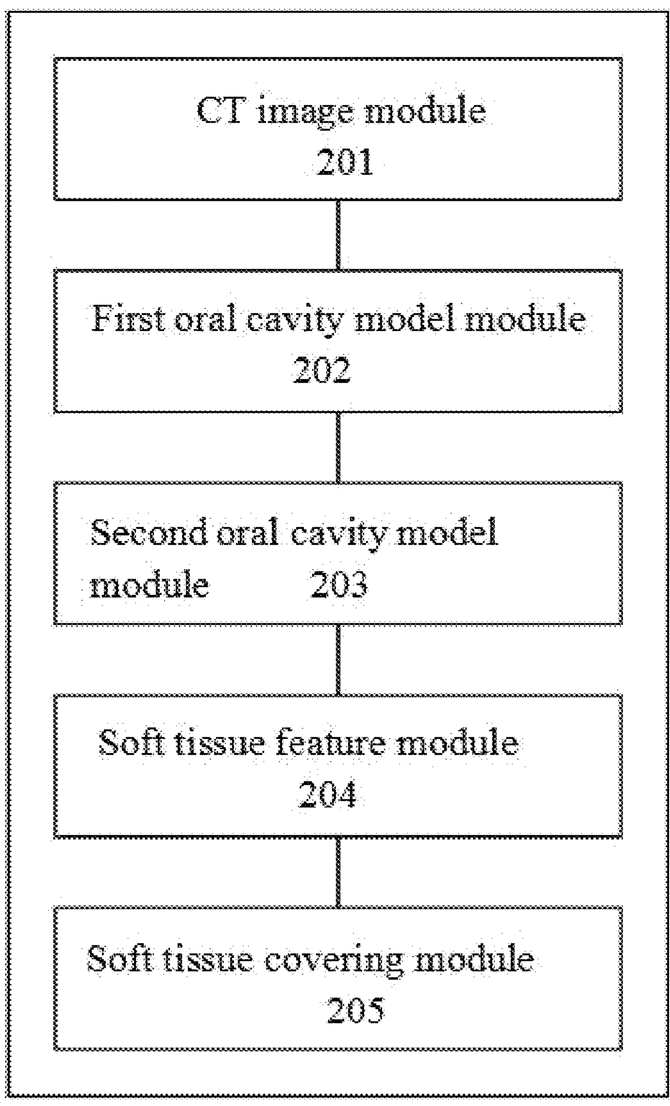
FIG. 4 shows a schematic structural diagram of a processing host provided by the embodiments of the disclosure.

Embodiment Two, referring to FIG. 3 and FIG. 4, a system for image generation based on oral imaging is provided, including an acquisition device 01 and a processing host 02; the acquisition device includes a cone-beam imaging device 011, a laser three-dimensional scanner 012 and an optical image acquisition device 013.

It should be noted that cone-beam imaging equipment 011 (cone-beam CT) is the most promising and practical equipment in oral skull imaging equipment today. Laser 3D scanner 012 is used to detect and analyze the shape (geometric structure) and appearance data (such as color, surface albedo and other properties) of objects or environments in the real world; as the main part of the three-dimensional laser scanning system, the three-dimensional laser scanner is composed of a laser emitter, a receiver, a time counter, a motor-controlled rotatable filter, a control circuit board and the like. The optical image acquisition device 013 includes, but is not limited to, an optical camera, an optical image detection sensor and an optical image collector also, an oral device for sensing various biological features, like temperature, pH, electromyographic signal, muscle thickness, blood flow status or other conditions in the oral cavity.

The processing host 02 includes a CT image module 201, a first oral cavity model module 202, a second oral cavity model module 203, a soft tissue feature module 204 and a soft tissue covering module 205.

The CT image module 201 is used for acquiring CT image data of an oral cavity to be treated and constructing an oral skeletal model according to the CT image data.

The first oral cavity model module 202 is used for extracting the skeletal features of the oral cavity skeletal model, and covering the oral cavity skeletal model with soft tissues according to the skeletal features through a preset oral cavity model database with healthy soft and hard tissues to obtain a first oral cavity model; where the preset oral cavity model database with healthy soft and hard tissues stores oral cavity models containing healthy soft and hard tissues.

The second oral cavity model module 203 is used for carrying out laser three-dimensional scanning on the oral cavity to be treated, so as to construct a second oral cavity model, and comparing the first oral cavity model with the second oral cavity model to obtain a soft tissue difference area between them and marking the soft tissue difference area in the second oral cavity model.

The soft tissue feature module 204 is used for acquiring optical image information of a target acquisition area in an oral cavity to be treated, and extracting soft tissue features from the optical image information; where the target acquisition area corresponds to the soft tissue difference area marked on the second oral cavity model.

The soft tissue covering module 205 is used for covering the extracted soft tissue features into the second oral cavity model to obtain a three-dimensional image model of the oral cavity to be treated and then acquiring oral images from the three-dimensional image model to generate oral images.

Optionally, acquiring CT image data of an oral cavity to be treated, and constructing an oral skeletal model based on the CT image data includes:

scanning the oral cavity to be treated layer by layer using a cone-beam imaging device according to the preset scanning interval to obtain CT image data corresponding to each layer;

carrying out skeletal hard tissue identification on CT image data corresponding to each layer, and extracting hard tissue feature model data corresponding to each CT image data;

sequentially correcting the hard tissue feature model data extracted from the corresponding CT image data of each layer, so that in the process of modifying the hard tissue feature model data of one layer each time, the hard tissue feature model data adjacent to the layer are taken as the modified reference model data, and the modified reference model data and the hard tissue feature model data of the layer are combined and merged, so as to calculate the first edge smoothness between the combined modified reference model data and the hard tissue feature model data of the layer, and then modify the hard tissue feature model data of the layer according to the first edge smoothness; and combining and merging the modified hard tissue feature model data of each layer to construct the oral skeletal model.

Optionally, modifying the hard tissue feature model data of the layer according to the first edge smoothness includes:

when the first edge smoothness is within the preset threshold interval, it is not necessary to modify the hard tissue feature model data of the layer;

when the first edge smoothness is out of a preset threshold interval, calculating a second edge smoothness between the hard tissue feature model data of each layer in the modified reference model data, and when the difference between the first edge smoothness and the second edge smoothness is great than a preset error, smoothing and modify the edge of the hard tissue feature model data of the layer according to the second edge smoothness, so as to complete the modification of the hard tissue feature model data of the layer; and repeating until the hard tissue feature model data of each layer is modified.

Optionally, extracting the skeletal features of the oral skeletal model, and covering the oral skeletal model with soft tissues based on the skeletal features through a preset healthy soft and hard tissue oral cavity model database to obtain a first oral cavity model includes:

extracting skeletal features of preset key areas in the oral skeletal model; where the preset key areas include the maxillary area, mandibular area, maxillary alveolar bone area and mandibular alveolar bone area;

in a preset healthy soft and hard tissue oral cavity model database, a soft and hard tissue oral cavity model with the greatest similarity to the skeletal features of the preset key area is retrieved as a reference model; where the healthy soft and hard tissue oral cavity model database prestores a plurality of different soft and hard tissue oral cavity models corresponding to the skeletal features of preset key areas; and extracting the soft tissue data of the reference model and overlaying the soft tissue data on the oral skeletal model to construct a first oral cavity model.

Optionally, carrying out laser three-dimensional scanning on the treated oral cavity to construct a second oral cavity model, and comparing the first oral cavity model with the second oral cavity model, so as to obtain the soft tissue difference area between the first oral cavity model and the second oral cavity model, and marking the soft tissue difference area in the second oral cavity model includes:

carrying out laser three-dimensional scanning on the oral cavity to be treated to obtain an oral cavity structure model;

matching the oral skeletal model with the oral cavity structure model to construct a second oral cavity model;

comparing the first oral cavity model with the second oral cavity model to sequentially obtain areas with different structures between the first oral cavity model and the second oral cavity model;

if the area of the different structure exists in the first oral cavity model, the area of the different structure is eliminated; and if the area of the different structure exists in the second oral cavity model, the area of the different structure is taken as a soft tissue different area and marked in the second oral cavity model.

Optionally, acquiring the optical image information of the target acquisition area in the oral cavity to be treated, and extracting the soft tissue features from the optical image information includes:

acquiring optical image information of the target acquisition area in the oral cavity to be treated, and sequentially carrying out pathological identification on the optical image information according to the pathological identification model; where the target acquisition area corresponds to the soft tissue difference area marked on the second oral cavity model; and identifying the optical image information with pathological features to identify the soft tissue features, so as to extract the soft tissue feature data with pathological features.

Optionally, covering the extracted soft tissue features in the second oral cavity model to obtain a three-dimensional image model of the oral cavity to be treated specifically includes:

covering the extracted soft tissue feature data with pathological features in a second oral cavity model at the corresponding area sequentially according to the target acquisition area of the optical image information with pathological features;

marking and eliminating the soft tissue difference areas corresponding to the optical image information without pathological features in the second oral cavity model to obtain the final second oral cavity model; and according to the soft tissue data in the first oral cavity model, the unlabeled areas in the final second oral cavity model are covered with soft tissue, so as to obtain a three-dimensional image model of the oral cavity to be treated.

Technical personnel in the field can clearly understand that for the convenience and simplicity of description, the specific working process of the system described above can refer to the corresponding process in the above-mentioned embodiments of the method and will not be repeated here.

Compared with the prior art, the embodiments of the disclosure have the following beneficial effects:

according to the technical schemes of the disclosure, the soft tissue difference area between the first and second oral cavity models is obtained by comparing the oral CT image data covered with soft tissue with the second oral cavity model obtained from laser three-dimensional scanning; and the soft tissue in the soft tissue difference area is covered with actual feature data by combining it with the optical image information, so that the three-dimensional image model of the oral cavity to be treated is accurately obtained, and the corresponding oral image is generated through the three-dimensional image model. This method avoids the collection and analysis of pathological soft tissues such as muscles and/or tumors only through optical images, resulting in the need for image splicing in the case of multiple optical image data, which is prone to image distortion; meanwhile, two-dimensional optical images cannot provide structural information of specific pathological soft tissues such as muscles and/or tumors, while the three-dimensional image model of the disclosure can accurately and clearly restore the structural information of the oral cavity to be treated, therefore, the disclosure has a high degree of reduction and is convenient for doctors to analyze the pathological conditions of the oral cavity.

Embodiment Three: correspondingly, the disclosure also provides a terminal device, including a processor, a memory and a computer program stored in the memory and configured to be executed by the processor, where the processor executes the method for image generation based on oral imaging according to any of the above when executing the computer program.

The terminal device of this embodiment includes a processor, a memory, and computer programs and computer instructions stored in the memory and executable on the processor. When the processor executes the computer program, it realizes the steps in Embodiment One, such as steps S101 to S105 shown in FIG. 1. Alternatively, when executing the computer program, the processor realizes the functions of each module/unit in the above system embodiments, such as the second oral cavity model module 203.

Illustratively, the computer program may be divided into one or more modules/units, which are stored in the memory and executed by the processor to complete the disclosure. The one or more modules/units can be a series of computer program instruction segments that can complete specific functions, and the instruction segments are used to describe the execution process of the computer program in the terminal device; for example, the second oral cavity model module 203 is used for carrying out laser three-dimensional scanning on the oral cavity to be treated, so as to construct a second oral cavity model, and comparing the first oral cavity model with the second oral cavity model, so as to obtain a soft tissue difference area between the two and mark it in the second oral cavity model.

The terminal device can be a computing device such as a desktop computer, a laptop, a handheld computer and a cloud server. The terminal device may include, but is not limited to, a processor and a memory. It can be understood by those skilled in the art that the schematic diagram is only an embodiment of a terminal device, and does not constitute a limitation on the terminal device, it may include more or less components than the schematic diagram, or combine some components or different components, for example, the terminal device may also include input and output devices, network access devices, buses, and the like.

The processor can be a central processing unit (CPU), other general processors, digital signal processor (DSP), disclosure specific integrated circuits (ASIC), field-programmable gate array (FPGA) or other programmable logic devices, discrete gates or transistor logic devices, discrete hardware components, etc. The general processor can be a microprocessor or any conventional processor, etc. The processor is the control center of the terminal equipment and connects all parts of the whole terminal equipment with various interfaces and lines.

The memory stores the computer programs and/or modules that enables the processor to perform various functions of the terminal device by running or executing computer programs and/or modules stored in the memory and calling data stored in the memory. The memory may mainly include a storage program area and a storage data area, where the storage program area may store an operating system, an application program required by at least one function, and the like; the storage data area may store data created according to the use of the mobile terminal and the like. In addition, the memory may include high-speed random-access memory, and may also include nonvolatile memory, such as hard disk, memory, plug-in hard disk, smart media card (SMC), secure digital (SD) card, flash card, at least one disk memory device, flash device, or other volatile solid-state memory devices.

The integrated module/unit of the terminal equipment can be stored in a computer-readable storage medium if it is realized in the form of a software functional unit and sold or used as an independent product. Based on this understanding, the disclosure can realize all or part of the processes in the methods of the above embodiments and can also be realized by instructing related hardware through a computer program, which can be stored in a computer-readable storage medium, and when executed by a processor, the computer program can realize the steps of the above methods. Where the computer program includes computer program code, which can be in source code form, object code form, executable files or some intermediate form, etc. The computer-readable medium may include any entity or device capable of carrying the computer program code, a recording medium, a USB flash drive, a removable hard disk, a magnetic disk, an optical disk, computer memory, Read-Only Memory (ROM), Random Access Memory (RAM), electric carrier signal, a telecommunication signal, software distribution medium, etc. It should be noted that The contents contained in the computer-readable medium can be appropriately increased or decreased according to the requirements of legislation and patent practice in the jurisdiction, for example, in some jurisdictions, according to legislation and patent practice, the computer-readable medium does not include electric carrier signals and telecommunication signals.

Embodiment Four: correspondingly, the disclosure also provides a computer-readable storage medium, the computer-readable storage medium includes a stored computer program; the computer program controls the device where the computer-readable storage medium is located while executing the method for image generation based on oral imaging according to any of the above embodiments.

The above-mentioned specific embodiments further explain the purpose, technical schemes and beneficial effects of the disclosure in detail. It should be understood that the above-mentioned embodiments are only specific embodiments of the disclosure and are not used to limit the protection scope of the disclosure. In particular, it is pointed out that any modification, equivalent substitution, improvement, etc. made within the spirit and principle of the disclosure should be included in the protection scope of the disclosure.

What is claimed is:

1. A method for image generation based on oral imaging, comprising:

acquiring CT image data of an oral cavity to be treated, and constructing an oral skeletal model based on the CT image data, wherein acquiring the CT image data of the oral cavity to be treated, and constructing the oral skeletal model based on the CT image data comprises:

scanning the oral cavity to be treated layer by layer by a cone-beam imaging device according to a preset scanning interval to obtain CT image data corresponding to each layer;

carrying out skeletal hard tissue identification on the CT image data corresponding to each layer, and extracting hard tissue feature model data corresponding to each CT image data;

sequentially modifying the hard tissue feature model data extracted from the corresponding CT image data of each layer, so that in the process of modifying the hard tissue feature model data of one layer each time, the hard tissue feature model data of at least one layer is taken as the modified reference model data, and the modified reference model data and the hard tissue feature model data of the layer are combined and merged, so as to calculate a first edge smoothness between the combined modified reference model data and the hard tissue feature model data of the layer, and then modify the hard tissue feature model data of the layer according to the first edge smoothness; and combining and merging the modified hard tissue feature model data of each layer to construct the oral skeletal model;

extracting skeletal features of the oral skeletal model, and covering the oral skeletal model with soft tissues based on the skeletal features through a preset healthy soft and hard tissue oral cavity model database to obtain a first oral cavity model; wherein the preset healthy soft and hard tissue oral cavity model database stores oral cavity models with healthy soft and hard tissues;

carrying out laser three-dimensional scanning on the oral cavity to be treated to construct a second oral cavity model, and comparing the first oral cavity model with the second oral cavity model, so as to obtain a soft tissue difference area between the first oral cavity model and the second oral cavity model, and then mark the soft tissue difference area in the second oral cavity model;

acquiring optical image information of a target acquisition area in the oral cavity to be treated, and extracting soft tissue features from the optical image information; wherein the target acquisition area corresponds to the soft tissue difference area marked on the second oral cavity model;

covering the extracted soft tissue features in the second oral cavity model to obtain a three-dimensional image model of the oral cavity to be treated, and then acquiring oral images from the three-dimensional image model to generate oral images; and wherein acquiring the optical image information of the target acquisition area in the oral cavity to be treated, and extracting soft tissue features from the optical image information specifically comprises the following steps: acquiring the optical image information of the target acquisition area in the oral cavity to be treated, and carrying out pathological identification on the optical image information in turn according to a pathological identification model; and identifying the soft tissue features of the optical image information with pathological features so as to extract the soft tissue feature data with pathological features.

2. The method for image generation based on oral imaging according to claim 1, wherein modifying the hard tissue feature model data of the layer according to the first edge smoothness comprises:

when the first edge smoothness is within a preset threshold interval, it is not necessary to modify the hard tissue feature model data of the layer;

when the first edge smoothness is out of the preset threshold interval, calculating a second edge smoothness between the hard tissue feature model data of each layer in the modified reference model data, and when a difference between the first edge smoothness and the second edge smoothness is great than a preset error, smoothing and modifying the edge of the hard tissue feature model data of the layer according to the second edge smoothness, so as to complete the modification of the hard tissue feature model data of the layer; and until the hard tissue feature model data of each layer is modified.

3. The method for image generation based on oral imaging according to claim 2, wherein extracting the skeletal features of the oral skeletal model, and covering the oral skeletal model with soft tissues based on the skeletal features through the preset healthy soft and hard tissue oral cavity model database to obtain the first oral cavity model comprises:

extracting skeletal features of preset key areas in the oral skeletal model; wherein the preset key areas comprise maxillary area, mandibular area, maxillary alveolar bone area and mandibular alveolar bone area;

in the preset healthy soft and hard tissue oral cavity model database, a soft and hard tissue oral cavity model with the greatest similarity to the skeletal features of the preset key area is retrieved as a reference model; wherein the healthy soft and hard tissue oral cavity model database prestores a plurality of different soft and hard tissue oral cavity models corresponding to the skeletal features of preset key areas; and extracting the soft tissue data of the reference model, and overlaying the soft tissue data on the oral skeletal model to construct the first oral cavity model.

4. The method for image generation based on oral imaging according to claim 3, wherein carrying out laser three-dimensional scanning on the oral cavity to be treated to construct the second oral cavity model, and comparing the first oral cavity model with the second oral cavity model, so as to obtain the soft tissue difference area between the first oral cavity model and the second oral cavity model, and marking the soft tissue difference area in the second oral cavity model comprises:

carrying out laser three-dimensional scanning on the oral cavity to be treated to obtain an oral cavity structure model;

matching the oral skeletal model with the oral structure model to construct the second oral cavity model;

comparing the first oral cavity model with the second oral cavity model to sequentially obtain areas with different structures between the first oral cavity model and the second oral cavity model; and if the area of the different structure exists in the first oral cavity model, the area of the different structure is eliminated; if the area of the different structure exists in the second oral cavity model, the area of the different structure is taken as a soft tissue different area and marked in the second oral cavity model.

* * * * *